(12) United States Patent
Gaharwar et al.

(10) Patent No.: US 10,898,445 B2
(45) Date of Patent: Jan. 26, 2021

(54) MINERAL-BASED NANOPARTICLES FOR ARTHRITIS TREATMENT

(71) Applicant: The Texas A&M University System, College Station, TX (US)

(72) Inventors: Akhilesh K. Gaharwar, Cypress, TX (US); James K. Carrow, College Station, TX (US)

(73) Assignee: The Texas A&M University System, College Station, TX (US)

( * ) Notice: Subject to any disclaimer, the term of this patent is extended or adjusted under 35 U.S.C. 154(b) by 113 days.

(21) Appl. No.: 16/060,273

(22) PCT Filed: Dec. 21, 2016

(86) PCT No.: PCT/US2016/068099
§ 371 (c)(1),
(2) Date: Jun. 7, 2018

(87) PCT Pub. No.: WO2017/112802
PCT Pub. Date: Jun. 29, 2017

(65) Prior Publication Data
US 2018/0360768 A1    Dec. 20, 2018

Related U.S. Application Data

(60) Provisional application No. 62/270,403, filed on Dec. 21, 2015.

(51) Int. Cl.
| | |
|---|---|
| *A61K 9/51* | (2006.01) |
| *A61K 9/00* | (2006.01) |
| *C08K 3/34* | (2006.01) |
| *A61K 9/14* | (2006.01) |
| *C12N 5/077* | (2010.01) |
| *A61K 35/28* | (2015.01) |
| *A61K 35/32* | (2015.01) |
| *B82Y 5/00* | (2011.01) |
| *B82Y 40/00* | (2011.01) |
| *A61K 47/69* | (2017.01) |

(52) U.S. Cl.
CPC .......... *A61K 9/5161* (2013.01); *A61K 9/0024* (2013.01); *A61K 9/14* (2013.01); *A61K 9/5115* (2013.01); *A61K 35/28* (2013.01); *A61K 35/32* (2013.01); *A61K 47/6923* (2017.08); *C08K 3/34* (2013.01); *C12N 5/0655* (2013.01); *B82Y 5/00* (2013.01); *B82Y 40/00* (2013.01); *C08K 2201/011* (2013.01); *C12N 2500/05* (2013.01); *C12N 2506/1353* (2013.01); *C12N 2533/10* (2013.01)

(58) Field of Classification Search
CPC ..... A61K 35/28; A61K 35/32; A61K 47/6923
See application file for complete search history.

(56) References Cited

U.S. PATENT DOCUMENTS

| | | | |
|---|---|---|---|
| 2014/0072720 A1 | 3/2014 | Watkins et al. | |
| 2017/0074861 A1* | 3/2017 | Singh | C12N 5/0012 |

FOREIGN PATENT DOCUMENTS

| | | | | |
|---|---|---|---|---|
| WO | WO-2014/205261 A1 | 12/2014 | | |
| WO | WO-2015/172073 A1 | 11/2015 | | |
| WO | WO-2015172073 A1 * | 11/2015 | ......... | G01N 33/5011 |

OTHER PUBLICATIONS

Kim et al (International Journal of Nanomedicine, Mar. 2015, vol. 10, pp. 2261-2272) (Year: 2015).*
Buchtova et al (Journal of Material Science—Materials in Medicine, 2013, DOI 10.1007/s10856-013-4951-0) (Year: 2013).*
Jorgenson et al (Stem Cells International, Mar. 2018, vol. 2018, pp. 1-16) (Year: 2018).*
Spiller et al (Tissue Engineering Part B Reviews, 2011, vol. 17, pp. 281-299). (Year: 2011).*
Popa et al (Biotechnology and Applied Biochemistry, 2012, vol. 59, pp. 132-141) (Year: 2012).*
Gaharwar, Akhilesh K. et al.; "Bioactive Silicate Nanoplatelets for Osteogenic Differentiation of Human Mesenchymal Stem Cells"; Advanced Materials; vol. 25; Jun. 25, 2013; pp. 3329-3336.
Carrow, James K. et al.; "Bioinspired Polymeric Nanocomposites for Regenerative Medicine"; Macromolecular Chemistry and Physics; vol. 216; Nov. 18, 2014; pp. 248-264.
Thakur, A. et al.; "Injectable Shear-thinning Nanoengineered Hydrogels for Stem Cell Delivery"; Nanoscale; vol. 8; Jun. 16, 2016; pp. 12362-12372.

* cited by examiner

*Primary Examiner* — Mark V Stevens
(74) *Attorney, Agent, or Firm* — Winstead PC

(57) ABSTRACT

Aspects of the invention are directed to mineral-based nanoparticles comprising silicate nanoparticles that induce human mesenchymal stem cells (hMSCs) into a cartilage-lineage through the upregulation of cartilage-specific genes resulting in the transformation of the cell phenotype into that of a chondrocyte, i.e., a cartilage producing cell. The silicate nanoparticles are synthesized through a process where the precipitate of sodium silicate is mixed with one or more elements and compounds and milled into nanoparticles.

12 Claims, 4 Drawing Sheets

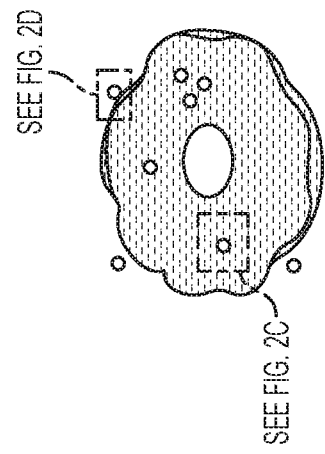
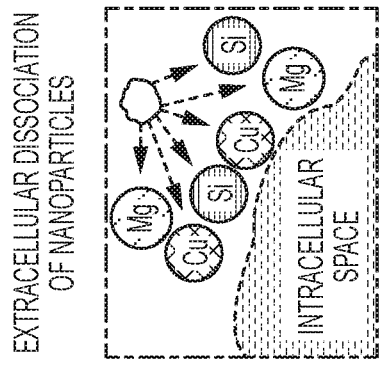
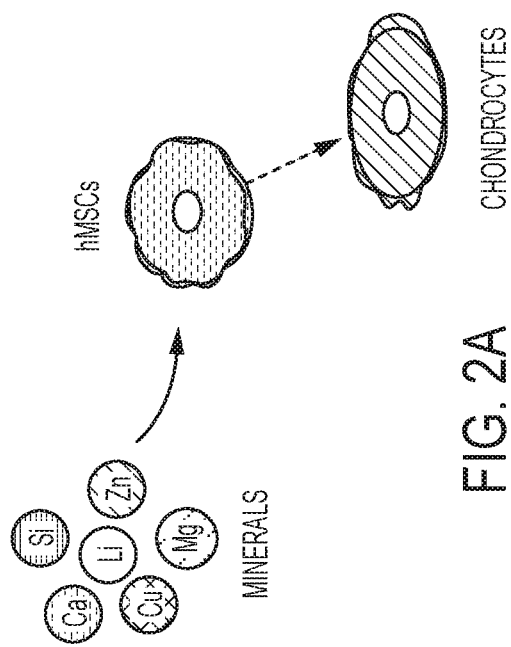
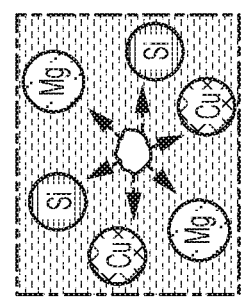

MINERAL-BASED NANOPARTICLES FOR ARTHRITIS TREATMENT

CROSS-REFERENCES TO RELATED APPLICATIONS

This application claims priority to and incorporates by reference the entire disclosure of U.S. Provisional Patent Application No. 62/270,403 filed on Dec. 21, 2015.

BACKGROUND OF THE INVENTION

Presently, there are very limited therapies to resolve cartilage damage within the joint. Autografts provide a functional tissue option, but can result in donor site morbidity. Additionally, clinicians have used supraphysiological doses of growth factors to stimulate cellular differentiation as well as cartilaginous production. However, such high concentrations have associated negative side effects like inflammatory responses, ectopic tissue formation, and potential tumor formation within the joint. For example, bone morphogenetic protein-2 (BMP-2) delivery via liposome encapsulation can induce cartilage formation at a defect site. However due to short half-life (7-16 minutes) and susceptibility to proteinases, administration of supraphysiological doses of BMP-2 is required to achieve therapeutic efficacy. Recent studies have highlighted a range of complications associated with the use of supraphysiological doses of BMP-2, including uncontrolled tissue formation, inflammation, neurological events, and carcinogenicity. Other growth factors currently investigated in preclinical studies such as transforming growth factor-beta1 (TGF-β1) have also shown limited clinical efficacy and have raised concerns, especially in relation to tumor growth, edema, and inflammatory responses. Other clinical approaches also include delivery of growth factors or extracellular matrix components such as glycoaminoglycans in the knee to stimulate cartilage growth. However, most of these approaches show limited ability for cartilage regeneration and are likewise associated with several side effects and high cost.

Ionic dissolution products from inorganic materials play an important role in controlling a variety of biological functions. Many elements such as silicon (Si), magnesium (Mg), lithium (Li), calcium (Ca), copper (Cu), or zinc (Zn) are present in the human body and their anabolic effects in metabolism are well known. Specifically, for cartilage synthesis, orthosilicic acid ($Si(OH)_4$) has been shown to enhance collagen synthesis and Ca metabolism via increasing serum Si levels. The role or potential impact of minerals in the realm of developmental biology has not yet been realized. Nanoparticles derived from these biocompatible components would therefore yield a means for localized delivery, intracellular uptake, and dissolution of bioactive minerals. Due to their mineral composition as well as unique physical characteristics, synthetic silicates afford a practical option for controlling stem cell behavior via direct cellular interactions or through a nanocomposite system. Therefore, bioactive materials that could provide an alternative means to regenerate cartilage tissue are of great interest.

SUMMARY OF THE INVENTION

An embodiment of the invention is directed to mineral-based nanoparticles comprising silicate nanoparticles that induce human mesenchymal stem cells (hMSCs) into a cartilage-lineage through the upregulation of cartilage-specific genes resulting in the transformation of the cell phenotype into that of a chondrocyte, i.e., a cartilage producing cell.

In an embodiment of the invention, nanoparticles are synthesized through a process where the precipitate of sodium silicate is mixed with one or more elements and compounds and milled into nanoparticles.

In another embodiment of the invention, nanoparticles are prepared for implantation by forming a nanocomposite either by placing the nanoparticles in growth media, or within a polymeric matrix. The nanocomposites prepared by either process may be functionalized with a variety of drugs or biological factors.

BRIEF DESCRIPTION OF THE DRAWINGS

FIG. 2A shows a diagrammatic representation of a cellular pathway stimulated by minerals;

FIG. 2B shows a diagrammatic representation of a human mesenchymal stem cell (hMSC);

FIG. 2C shows a diagrammatic representation of the intracellular dissociation of minerals from a silicate nanoparticle;

FIG. 2D shows a diagrammatic representation of the extracellular dissociation of minerals from a silicate nanoparticle;

FIG. 3B—pH 7.4; FIG. 3C—pH 10) evaluated using Inductively Coupled Plasma-Mass Spectrometry (ICP-MS);

DESCRIPTION OF EXEMPLARY EMBODIMENTS

Figure 1:
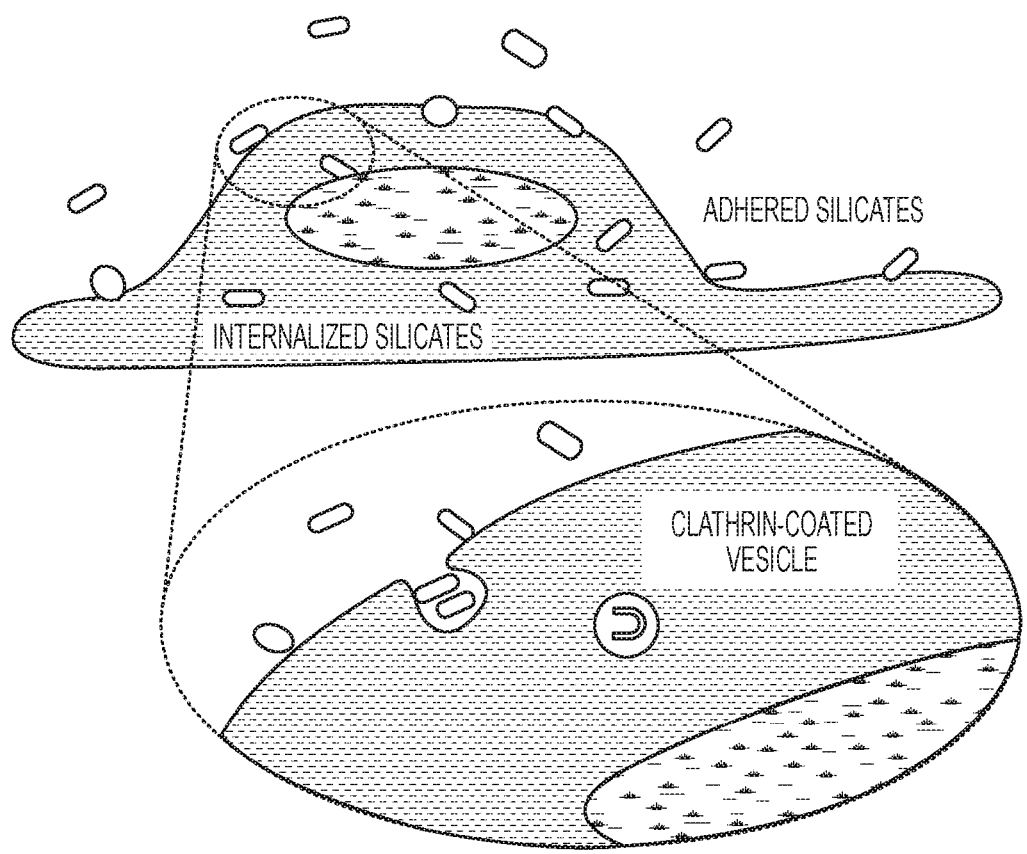
FIG. 1 shows a diagrammatic representation of general cellular interactions with nanosilicates mediated by clathrin vesicles to distribute the nanosilicates within the cell.

Embodiments of the claimed invention are directed to a mineral-based nanoparticle composition comprising silicate nanoparticles that promote the induction of human mesenchymal stem cells (hMSCs) into a cartilage-lineage. Specifically, the silicate nanoparticles upregulate cartilage-specific genes and produce a proteoglycan and glycosaminoglycan rich extracellular matrix in order to transform the cell phenotype into that of a chondrocyte, i.e., a cartilage-producing cell. The size, charge, shape, and ionic composition of these nanoparticles enable positive interactions with surrounding cells, while also stimulating a chondrogenic effect.

Silicate nanoparticles are cytocompatible with predictable degradation rates and degradation products. These degradation products are already present in the body, and thus do not present problems with systemic clearance. Cells may generate a dose-dependent response to the nanoparticles to produce a proteoglycan rich matrix outside of the cell.

In an embodiment of the invention, silicate nanoparticles that are to be introduced to induce stem cells to transform chondrocytes, are placed in growth media along with the stem cells. In other embodiments, the silicate nanoparticles are placed within a polymeric matrix to form a stable nanocomposite material. In certain embodiments, the stable nanocomposite material made by either of the above methods is functionalized with a variety of drugs or biological factors for enhanced regenerative medicine therapies. In certain embodiments of the invention, the nanoparticles may be directly injected into the intra-articular space of a subject to stimulate cartilage regeneration.

In certain embodiments, silicate nanoparticles may be utilized as carriers to deliver therapeutics to a subject. The advantage of utilizing silicate nanoparticles as carriers of therapeutics is that the silicate nanoparticles deliver the therapeutics over a prolonged period of time. In certain embodiments, one or more biologics may be co-delivered with silicate nanoparticles to obtain synergistic effect.

In certain embodiments of the claimed invention, silicate nanoparticles are used to construct devices such as injectable tissue repair matrixes, bioactive fillers and carriers for intracellular or extracellular deliveries. Other embodiments of the claimed invention are directed to other tissue and cell types such as bone regeneration.

An embodiment of the claimed invention is directed to the synthesis of mineral-based nanoparticles utilizing salts of sodium, magnesium, orthosilicic acid, and lithium with sodium silicate added at controlled rates and temperatures to yield a precipitate, treating the precipitate at high temperature for crystallization so that it may be filtered, washed, dried, and milled into nanoparticles, and lastly filtered and sterilized using a 0.2 μm filter and ultraviolet (UV) light. In certain embodiments, the nanoparticles may be incorporated into polymeric solutions to form a hydrogel, a solid scaffold, or electrospinning scaffold. In certain embodiments, solutions composed of up to 5% (w/v) silicate nanoparticles can be mixed with varying amounts of polymer in a variety of solvents. These polymer solutions may then be crosslinked into a determined shape via a mold and seeded with stem cells or chondrocytes for further implantation into the joint space.

In certain embodiments of the claimed invention, synthetic silicate nanoplatelets containing $SiO_2$ (59.5%), MgO (27.5%), $Na_2O$ (2.8%) and LiO (0.8%) with low heavy metals content are used. In certain embodiments, example of synthetic silicate nanoplatelets include, but are not limited to, laponite, montmorillonite, hectorite, saponite, kaolinite, palygorskite, and sepiolite. The specific surface area of silicate nanoplatelets was 370 $m^2/g$ and bulk density of 1 $mg/cm^3$. Bone marrow-derived human mesenchymal stem cells used in certain embodiments of the invention are grown in normal growth media (α-MEM with 16.5% FBS and 1% pen/strep). The cells are cultured until 65-75% confluency and were used before passage 5 for all experiments. The cells are trypsinized and seeded in 96-well plates at a density of 4000 cells/well in normal growth media. After cells reach ~70% confluency, various concentrations of silicates are added to new normal growth media. Cells are kept in the presence of silicates for 24 hours and then the media is replaced again with normal media lacking silicates. Cells are fed every 3-4 days.

In an embodiment of the claimed invention, the viability of the claimed invention for regenerative medicine applications was assessed. Cell interactions with the silicate nanoparticles were monitored. Due to the role that pH may have on mineral dissolution and therefore bioactivity, nanoparticle uptake was evaluated. Various endocytic pathways were blocked using three individual drugs and the fate of fluorescently-tagged nanoparticles was monitored via flow cytometry (FIG. 1). Fluorescence was significantly reduced after treatment with a clathrin-mediated inhibitor drug and shifted toward the negative control of cells lacking nanoparticle treatment, thereby highlighting the primary pathway for nanoparticle uptake into the cell. Once the particles entered the cell, dose-dependent biocompatibility was evaluated via cell cycle analysis. Cell cycle analysis demonstrated no adverse effects at relevant bioactive concentrations (up to 1 mg/mL).

Due to the ability of the nanosilicates to rapidly interact with hMSCs, they remain cytocompatible after internalization, and dissolve into bioactive mineral components. Therefore, they have the potential to manipulate the phenotype of the stem cells, specifically into the chondrogenic lineage. Proteoglycan synthesis was monitored after a 24 hour treatment with various nanoplatelet concentrations in normal media conditions. The normal growth media is maintenance media that does not trigger differentiation of hMSCs. After 14 days without any additional growth factors, cells treated with a concentration of 100 μg/mL displayed significantly more staining for sulfated proteoglycans, representative of successful induction into the chondrogenic lineage. The silicate nanoplatelets display an inherent bioactivity that can be utilized for controlling cell behavior for tissue engineering applications. This bioactivity emanates from synergistic minerals combined within a single particle. In certain embodiments, the synergistic minerals are magnesium, orthosilicic acid, and lithium.

To further demonstrate the clinical feasibility in a regenerative capacity of these materials, silicate nanoplatelets were entrapped within a polymeric matrix. FIG. 2 shows a mechanism of SiNP bioactivity with hMSCs resulting in a variety of tissue-specific lineages and cellular outcomes. The extracellular and intracellular dissociation of minerals from the nanoparticle in aqueous environments results in local delivery of relevant minerals, potentially motivating changes in cell phenotype. hMSCs are encapsulated within a three-dimensional (3D) microenvironment to motivate chondrogenic differentiation. Kappa-Carrageenan (kCa) was utilized to generate a 3D construct due to its similarity to the extracellular matrix present in native cartilage as well as lacks intrinsic recognizable cellular sites that could facilitate binding or spreading. This characteristic maintains a round cellular morphology, which has been shown to cultivate induction into a chondrocyte lineage. Therefore, a nanocomposite of bioactive synthetic silicates within a kappa-carrageenan polymeric matrix (kCa-S) was fabricated as an implantable hydrogel for cartilage regeneration. To verify successful cartilage protein deposition, sulfated glycosaminoglycan (sGAG) staining was again completed after 14 days and hydrogel images were analyzed to quantify extent of staining. Results displayed a significant enhancement in scaffold bioactivity after impregnation with silicate nanoplatelets as confirmed by increased proteoglycan staining. This suggests that the presence of bioactive minerals in the form of the synthetic silicates further stimulates chondrogenic pathways within hMSCs to provide a useful nanocomposite system for cartilage regeneration.

The unique interactions between the silicate nanoparticles and polymers or solvents facilitate injectable, minimally invasive therapies that aid in the regenerative process via active cellular stimulation or by locally delivering bioactive factors.

Genetic and phenotypic alterations in cell behavior following mineral-based nanoparticle treatment were evaluated. There is increasing evidence that ionic dissolution products from inorganic materials also play an important role in controlling cell fate. Many naturally occurring minerals such as magnesium (Mg), silicon (Si), lithium (Li), copper (Cu), or zinc (Zn) are present in the human body and their impact on metabolism are well known. For example, Si is essential for metabolic processes, angiogenesis during bone regeneration, and calcification of bone tissue. Ortho-silicic acid ($Si(OH)_4$) promotes collagen type I synthesis and osteoblast differentiation via Wnt/β-catenin signaling pathway. Wnt signaling is implicated in osteogenic differentiation of stem cells and can be likewise stimulated by the presence of strontium (Sr). $Mg^{2+}$ is shown to stimulate new bone formation, and increases bone cell adhesion and stability by facilitating the interactions with integrins. $Li^+$, an inhibitor of glycogen synthetase kinase-3β (GSK-3β), activates Wnt-responsive genes by elevating cytoplasmic β-catenin, and Wnt signaling in turn stimulates osteogenesis as well as glycosaminoglycan synthesis in vivo and in vitro, respectively. Significant amounts of cellular $Cu^{2+}$ are found in human endothelial cells when undergoing angiogenesis. Additionally, $Cu^{2+}$ has shown to stimulate proliferation of human endothelial cells and also induces differentiation of mesenchymal cells towards the osteogenic lineage. $Zn^+$ is shown to have anti-inflammatory effect and stimulates bone formation in vitro by RUNX2 activation in osteoblasts. $Zn^+$ is also shown to increases ATPase activity, and regulates transcription of osteoblastic differentiation genes, such as collagen I, ALP, osteopontin and osteocalcin.

As indicated above, mineral ions have been shown to induce osteogenesis, angiogenesis, and synthesis of cartilage-specific extracellular matrix; therefore, via appropriate design of nanomaterials, complex tissue organization can be developed.

Figures 3A, 3B, 3C:
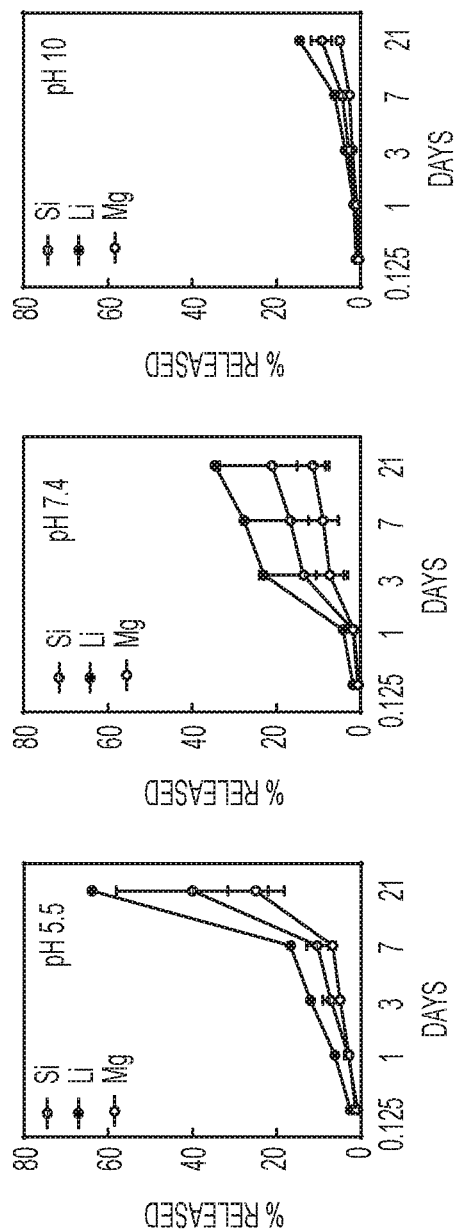
FIGS. 3A, 3B and 3C show a mechanism of SiNP bioactivity with hMSCs with mineral dissolution and release from nanoparticle under physiologically relevant pHs (FIG. 3A—pH 5.5.

A mechanism of induction involves the dissolution of the bioactive minerals from the nanoparticle in the local cell environment. FIG. 3 shows the mineral dissolution and its release from the silicate nanoparticle under physiologically relevant pH ranges evaluated using Inductively Coupled Plasma-Mass Spectrometry (ICP-MS). Results indicate a potential for maximum release of bioactive minerals within endocytic vesicles (pH 5.5), with lower release expected in the extracellular space (pH 7.4). The successful release of these minerals in the extracellular and intracellular space result in the transformation of cell phenotype into that of a chondrocyte. The presence of the individual or combined ionic components, specifically magnesium ($Mg^{2+}$), lithium ($Li^+$), and orthosilicic acid ($Si(OH)_4$), in the extracellular space (pH ~7.4) or intracellular vesicles (pH ~5.5) may drive this transformation of hMSC behavior to achieve the desired chondro-lineage. Results indicate a potential for maximum release of bioactive minerals within endocytic vesicles (pH 5.5), with lower release expected in the extracellular space (pH 7.4). The successful release of these minerals in the extracellular and intracellular space result in the transformation of cell phenotype into that of a chondrocyte.

Hyperspectral imaging, which enables visualization of internalized nanomaterials via collecting optical and spectrophotometry data, was utilized to monitor distribution of nanosilicates within the cell body. After nanosilicate mapping to images using their distinct spectral profile, uptake throughout the cell body was confirmed. This approach allowed for imaging of internalized nanosilicates without chemical conjugation, thereby eliminating any potential to modify internalization mechanisms. Fluorescently-labeled nanosilicates were applied to 2D cultured hMSCs at various concentrations for 15 minutes and flow cytometry monitored fluorescence of individual cell events. Results indicated a linear correlation of fluorescence intensity with concentration ($R^2$=0.996).

The mechanism behind internalization events was evaluated using chemical inhibition of various endocytic pathways, specifically that of clathrin-mediated, caveolar-mediated, and macropinocytosis using chlorpromazine hydrochloride, nystatin, and wortmannin, respectively. A significant decrease was observed in fluorescence uptake by cells treated with a clathrin-inhibitor (79.5% reduction), while additional endocytic mechanisms played a less prominent role in nanosilicate uptake. Furthermore, nanosilicate-cell membrane binding and subsequent uptake occurred over rapid timescales and saturated after 10-15 minutes in agreement with clathrin vesicle dynamics. These results demonstrate that the nanosilicates enter the cell body through cell mediated mechanisms, enabling the localization of these bioactive particles inside of the cell. Likewise, the results corroborate the hypothesis that the physical characteristics of the nanosilicates facilitate the positive interactions with the surrounding cells, thereby leading to a chondrogenic response.

To evaluate transcriptome alterations following human mesenchymal stem cell (hMSC) treatment with various bioactive nanomaterials, RNA Sequencing (RNA-Seq) can provide a high-throughput, comprehensive analysis technique to monitor transcriptome variability between cell populations exposed to specific microenvironments. Furthermore, the breadth of coverage of this technique provides a measure of gene expression for predicted and unanticipated targets, which can elucidate previously unknown molecular pathways.

The claimed method of using nanosilicates also lends itself to the quantitative evaluation of the differentiation capacity of bioactive nanomaterials. Therefore, this technology has the potential to drive the development of functional nanomaterials for regenerative medicine via genomic insight as has been the case for reducing cytotoxicity of nanomaterials. While single-cell phenotypes do not necessarily follow a snapshot of gene expression at a specific moment in time considering many signaling pathways are stochastic, whole-transcriptome analyses enable broad insight of population-wide genetics with great sensitivity, enabling the formation of more complete gene networks.

Figure 4:
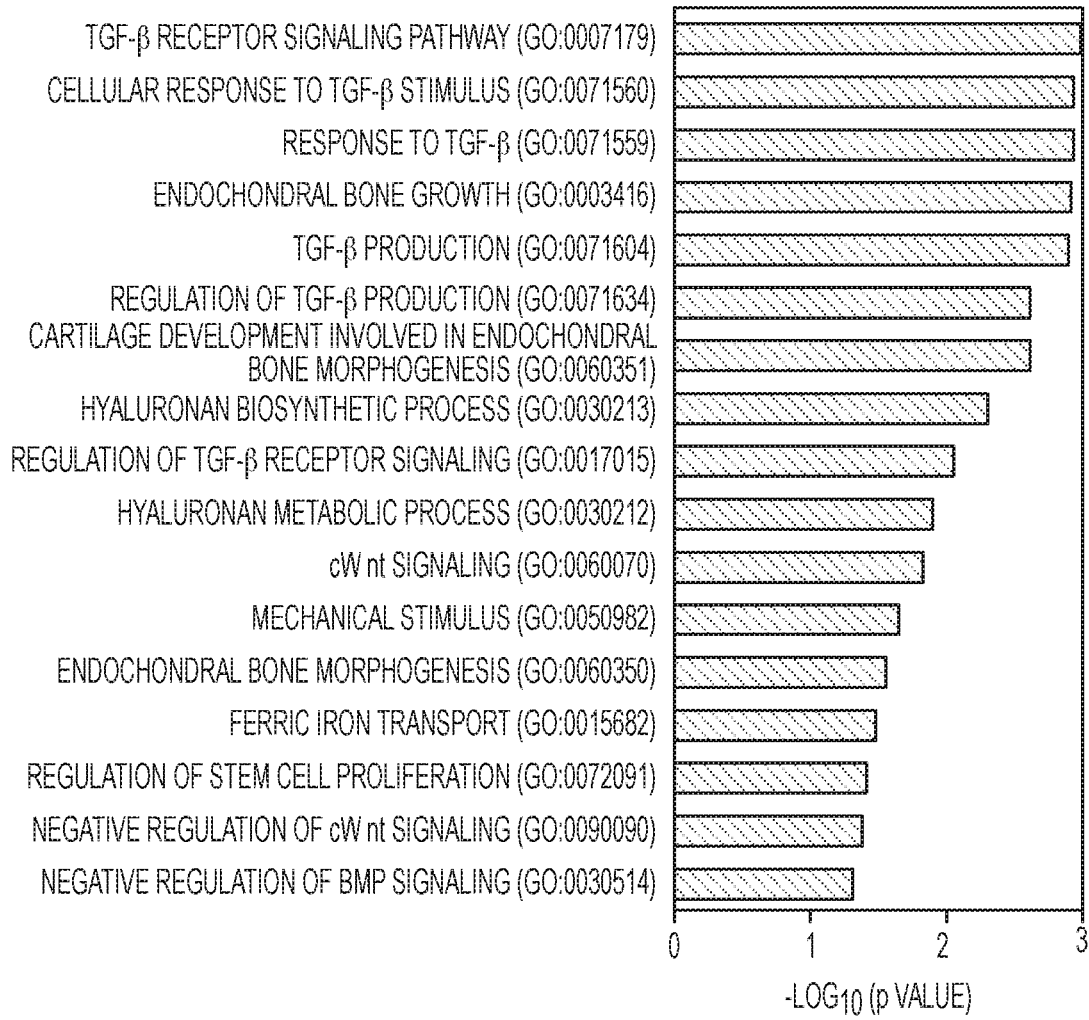
FIG. 4 shows a GO family plot demonstrating significant changes to genes annotated to chondrogenic-related pathways.
Figure 5:
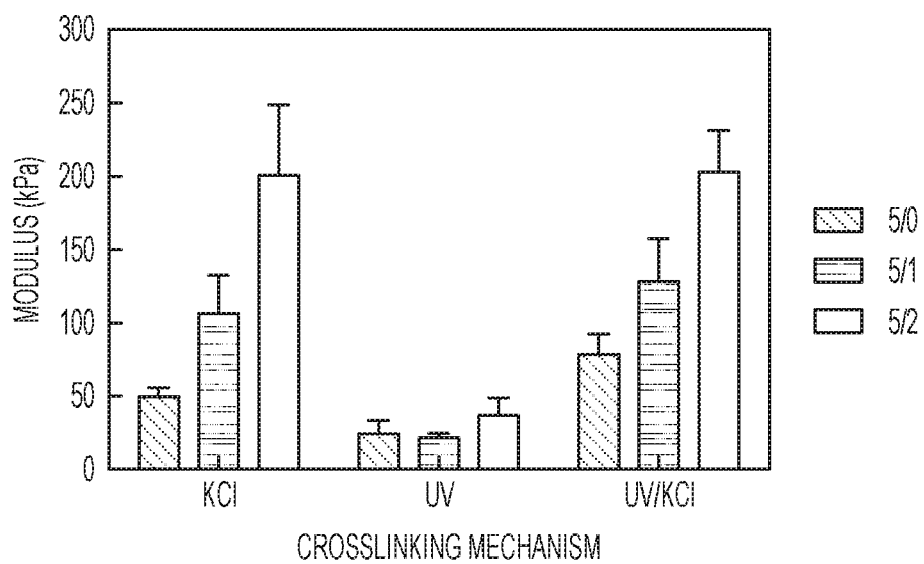
FIG. 5 shows the enhanced mechanical properties of hydrogels by the addition of silicate nanoparticles under a variety of cross-linking conditions.

The potential of the mineral-based nanoparticles for cartilage engineering was assessed from a genetic perspective using ribonucleic acid-sequencing (RNA-Seq). This technique enables the discovery of sensitive gene expression across the whole transcriptome of the cell, specifically human mesenchymal stem cells (hMSCs). Following sequencing of genes from cells lacking nanosilicate treatment as well as treated cells (concentration 50 µg/mL in growth media, 24 hr treatment, 7 days of culture), statistical analysis software was employed to compare and discern genetic targets that exhibited statistically significant changes in levels of expression. Analysis of these two cell populations indicated a robust change in cell behavior, including that of a chondrogenic response. The evaluation of both individual genes and gene ontology terms (GO terms) pertaining to related cellular pathways uncovered cartilage-specific shifts in behavior. FIG. 4 shows a GO family plot demonstrating significant changes to genes annotated to chondrogenic-related pathways; In addition to upregulation of relevant ECM components (e.g. Hyaluronan), stem cells indicate a sensitivity toward TGF-β stimulus and production, providing a means of synergistic activation of chondrogenic pathways and enhanced tissue formation.

GO terms pertaining to the cartilage regenerative outcome (e.g. chondrocyte differentiation [GO:0002062], hyaluronan biosynthetic process [GO:0030213], and cartilage development involved in endochondral bone morphogenesis [GO: 0060351]) demonstrated the transformative potential of nanosilicates in regards to cellular signaling pathways. Likewise, significant upregulation of chondro-related genes like cartilage oligomeric matrix protein (COMP, $\log_2$fold change: 2.238, $p_{adj}$: 9.34E-182), aggrecan (ACAN, $\log_2$fold change: 1.004, $p_{adj}$: 1.69 E-9), hyaluronan synthase 1 (HAS1, $\log_2$fold change: 1.08, $p_{adj}$: 3.4 E-16), and transforming growth factor, beta 1 (TGFβ1, $\log_2$fold change: 0.418, $p_{adj}$: 1.21E-6) was noted. These results demonstrate the direct induction potential of nanosilicates for cartilage engineering. However, a multitude of supplementary GO terms illustrate an alternative mechanism to drive lineage specific regeneration following nanosilicate treatment, specifically those regarding cellular responses to growth factor stimulus [GO:0071363] in general or even specific growth factors like TGF-β [GO:0071560]. These families of stimulated genetic targets highlight a potential secondary route to control cell behavior by priming hMSCs with nanosilicates for subsequent growth-factor stimulation. This enables the utilization of reduced growth-factor concentrations in tissue engineering constructs for the regeneration of cartilage throughout the body. Nanosilicates could likewise be utilized as a delivery vehicle for these bioactive molecules, thereby providing simultaneous stimulation toward cartilage-specific lineages.

An embodiment of the claimed invention is directed to creating a three-dimensional (3D) microenvironment as seen in native cartilage. In order to accomplish this, hMSCs are cultured and centrifuged into a 3D pellet. The capability to form these cellular-based structures in the presence of mineral-based nanoparticles will enable more clinically relevant treatment of stem cells or chondrocytes to take place. The feasibility of utilizing these culture conditions in the presence of silicate nanoparticles has been investigated and it has been found that these 3D structures remain stable in growth media for over 21 days of culture. Additionally, the chondrogenic phenotype is maintained in pellet culture following silicate treatment. The formation of glycosaminoglycan (GAGs) in pellet culture was also observed which further demonstrates the differentiation of hMSCs into chondrogenic phenotype.

Because of their ability to mimic the extracellular matrix (ECM) as well as restrain imbedded nanoparticles and growth factors, hydrogels are an attractive option for tissue engineering scaffolds. Their high water content and diffusion kinetics also allow for cell encapsulation during fabrication, which can expedite the tissue regeneration process as the stem cells required for tissue generation would already be located in the defect site. The nanosilicates endue the polymeric matrix with shear-thinning qualities due to the physical electrostatic interactions and weak chemical forces (e.g. hydrogen-bonding) between the surfaces of the particles and polymer chains. In terms of scaffold composition, a hydrogel utilizing a polysaccharide similar to that found in native cartilage, kappa Carrageenan, was suitable for cartilage engineering. The inherent induction stimuli presented by the scaffold material, due to its lack of cellular binding sites to promote chondrocyte-like morphologies and mechanical properties, promotes chondrogenic differentiation in conjunction with embedded mineral-based nanoparticles. This polymer can also be chemically modified to achieve responsiveness to UV stimulation, thereby providing a secondary mechanism of crosslinking.

For 2% and 5% modified kappa Carrageenan hydrogels, addition of either 1% or 2% (by weight) silicate nanoparticles enhanced the mechanical properties of the hydrogels under a variety of crosslinking conditions. Cyclic compression was utilized to characterize hydrogel resilience using energy dissipation as a quantitative measure. Results indicate a dual crosslinking mechanism as an optimal means to achieve resilience while maintaining strength comparable to that of native cartilage (FIG. 6). Additionally, following UV crosslinking, rheological analysis confirmed stability of nanocomposites over ranges of stresses and oscillatory frequencies, while indicating highly controllable strength through simple variations of polymer (2% or 5% by weight) or nanoparticle concentration (0%, 1%, or 2% by weight). These gels can be manipulated easily to fill any cartilage defect site through direct injection and crosslinking in vivo, printed to specified dimensions, or using predefined molds.

Conditional language used herein such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. A method of treating cartilage damage within a joint, preparing a mineral-based nanoparticle composition comprising silicate nanoparticles prepared from salts of magnesium, orthosilicic acid and lithium and wherein the silicate nanoparticles contain magnesium, orthosilicic acid and lithium;
placing the nanoparticle composition in close proximity to human mesenchymal stem cells; and
inducing the stem cells to form chondrocytes, wherein the silicate nanoparticles cause the increased expression of genes for at least one of cartilage oligomeric matrix protein, aggrecan and hyaluronan synthase I.

2. The method of claim 1, wherein upregulating cartilage-specific genes produces a proteoglycan and glycosaminoglycan rich extracellular matrix.

3. The method of claim 1, wherein upregulating cartilage-specific genes results in the transformation of the stem cell into a chondrocyte.

4. The method of claim 1, wherein the size, charge, shape, and ionic composition of the nanoparticle composition enables positive interactions with surrounding cells and stimulates a chondrogenic effect.

5. The method of claim 1, wherein the concentration of the silicate nanoparticles is no greater than 5% (w/v) of the nanoparticle composition.

6. The method of claim 1, wherein the nanoparticle composition is a hydrogel, a solid scaffold or an electrospun scaffold.

7. The method of claim 1, wherein the silicate nanoparticles further comprise one or more of magnesium oxide, silicon dioxide, sodium oxide, lithium oxide, and/or sodium silicate.

8. The method of claim 1, wherein the silicate nanoparticles comprise one or more of laponite, montmorillonite, hectorite, saponite, kaolinite, palygorskite, and/or sepiolite.

9. The method of claim 1, wherein placing the nanoparticle composition in close proximity to human mesenchymal stem cells comprises directly injecting the nanoparticle composition into intra-articular space of a subject.

10. The method of claim 1, wherein placing the nanoparticle composition in close proximity to human mesenchymal stem cells comprises encapsulating the stem cells in a three-dimensional microenvironment.

11. The method of claim 1, wherein the nanoparticle composition further comprises one or more therapeutics.

12. The method of claim 10, wherein the three-dimensional microenvironment comprises Kappa-Carrageenan.

* * * * *